United States Patent [19]

Witzel et al.

[11] Patent Number: 5,434,291
[45] Date of Patent: Jul. 18, 1995

[54] PREPARATION OF AMINOPROPIONITRILES

[75] Inventors: Tom Witzel, Ludwigshafen; Rudolf Kummer; Franz Merger, both of Frankenthal; Guido Voit, Schriesheim; Martin Brudermueller, Mannheim; Claus-Ulrich Priester, Ludwigshafen; Wolfgang Harder, Weinheim, all of Germany

[73] Assignee: BASF Aktiengsellschaft, Germany

[21] Appl. No.: 251,334

[22] Filed: Jun. 1, 1994

[30] Foreign Application Priority Data

Jun. 28, 1993 [DE] Germany .................. 43 21 273.5

[51] Int. Cl.⁶ .................................. C07C 253/30
[52] U.S. Cl. .................................. 558/452
[58] Field of Search .......................... 558/452

[56] References Cited

U.S. PATENT DOCUMENTS

| | | | |
|---|---|---|---|
| 1,992,615 | 8/1932 | Hoffmann et al. | 558/452 X |
| 2,401,429 | 8/1942 | Küng | 260/464 |
| 2,432,511 | 2/1943 | Davis et al. | 260/464 |
| 2,448,013 | 8/1948 | Buc et al. | 558/452 |
| 2,742,491 | 4/1956 | Weijlard et al. | 260/465.5 |
| 2,819,303 | 1/1958 | Griffith et al. | 260/534 |
| 3,174,992 | 3/1965 | McCracken | 260/465.5 |
| 3,914,280 | 10/1975 | Yamakami et al. | 260/465 X |
| 3,935,256 | 1/1976 | Verbeeck | 260/534 A |
| 4,211,725 | 7/1980 | Kluger et al. | 260/583 P |
| 4,965,362 | 10/1990 | Merger et al. | 546/246 |
| 5,247,120 | 9/1993 | Merger et al. | 558/452 |

FOREIGN PATENT DOCUMENTS 1003740  8/1957  Germany .
642409   9/1950  United Kingdom .

OTHER PUBLICATIONS

Bruson, Organic Reactions, vol. 5, (Dec. 1949), pp. 82, 83, 113.
Cyanamid, The Chemistry of Acrylonitrils, 2nd Ed., (1959), p. 155.
J. Chem. Soc., pp. 1369 and 1371, presented 9(1947); Goldberg, et. al.
Chem. Abstr. vol. 83 26879g (Jul. 1975), Khohhlov, et. al.
Org. Syn. vol. 27, pp. 3 and 5, presented 4 (1947).
Przemyst. Chem., vol. 44(2) 85–86 (Feb. 1965), Szlompek-Nesteruk.

Primary Examiner—Joseph Paul Brust
Attorney, Agent, or Firm—John H. Shurtleff

[57] ABSTRACT

A process for the preparation of aminopropionitriles of the general formula I

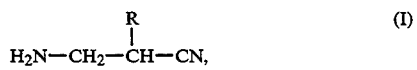

in which R denotes hydrogen or methyl, wherein ammonia is caused to react with an acrylonitrile of the general formula II

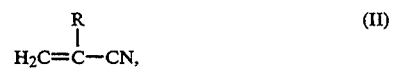

In which the substituent has the aforementioned meanings, in a molar ratio of from 1:1 to 500:1 over a heterogenic catalyst at temperatures ranging from 40° to 180° C. and pressures ranging from 10 to 350 bar.

12 Claims, No Drawings

PREPARATION OF AMINOPROPIONITRILES

The present invention relates to a new and improved process for the preparation of aminopropionitriles by the reaction of excess ammonia with acrylonitriles over heterogenic catalysts at elevated temperatures and pressures.

*J. Chem. Soc.*, 1369 to 1371 (1947) describes the reaction of ω-bromoalkyl cyanides with the potassium salt of the phthalimide and the following reaction with hydrazine hydrate. However, this process is unsuitable for the industrial preparation of 3-aminopropionitrile however.

U.S. Pat. No. 3,174,992 reveals the reaction of ethylenecyanohydrine with ammonia over moist Raney-nickel at temperatures near 100° C. under autogenous pressure. The reaction is unsatisfactory since it produces a yield of only 54%.

3-Aminopropionitrile and bis(2-cyanoethyl)amine are also obtained in an unfavorable ratio of 2:1 via the technically expensive indirect route involving 2-methoxypropionitrile by reaction with ammonia in the presence of Raney cobalt at temperatures ranging from 65° to 80° C. under a pressure of 165 bar, as described in DE-A 1,003,740.

As regards the preparation of 3-aminopropionitrile by the direct reaction of acrylonitrile with ammonia it is known that anhydrous ammonia does not react with acrylonitrile at room temperature, but can be used rather as a stabilizer for acrylonitrile (U.S. Pat. No. 2,432,511). U.S. Pat. No. 2,401,429 discloses that after a period of 2 days the reaction of acrylonitrile with liquid ammonia at room temperature yields, in addition to 76% of bis(2-cyanoethyl) ether, 11% of 3-aminopropionitrile. At 90° C., acrylonitrile, when caused to react with liquid ammonia under pressure, yields, inter alia 12.5% of 3-aminopropionitrile (DE-A 598,185).

Furthermore, it is known that the addition of protic solvents has an advantageous effect on the chemical addition of NH$_3$ to acrylonitrile. The addition of steam to the acrylonitrile-ammonia mixture is described, for example, in *Chem. Abstr.* Vol. 83, 26,879. Usually however, aqueous ammonia is used at temperatures ranging from 80° to 130° C. At a ratio of ammonia:acrylonitrile:-water of from 5 to 15:1:5 to 20 there is obtained 3-aminopropionitrile besides bis(2-cyanoethyl)amine in yields of from 57 to 80% (eg U.S. Pat. No. 3,935,256—62%, DE-A 2,436,651—70%, U.S. Pat. No. 2,448,013—78%, U.S. Pat. No. 2,819,303—59%, *Org. Syn.* 27, 3 to 5 (1947)—57%).

Drawbacks of these processes using aqueous ammonia become apparent during subsequent processing of the mixture of products Ü
- removal, by distillation, of added water during the circulation necessary as a consequence of the high ammonia concentrations
- selectivity losses toward 3-aminopropionitrile during separation of ammonia/water
- hydrolysis of the nitrile groups—damage to the catalyst during the following hydrogenation.

*Przemyst. Chem.* 44(2), 85 (1965) and GB-A 642,409 reveal processes in which the addition of from 15 to 20 equivalents of methanol produces a yield of 81% of 3-aminopropionitrile. The formation of by-products by methylation has a prohibitive effect on industrial utilization of the processes. A yield of 68% of 3-aminopropionitrile is obtained, on the other hand, when 3 equivalents of tert-butanol are added (U.S. Pat. No. 2,742,491).

The preparation of 3-aminopropionitrile by aminolysis of bis(2-cyanoethyl)amine mit ammonia, as described in DE-A 2,436,651, demands temperatures of from 130° to 170° C. and proceeds very slowly with reaction times ranging up to 165 min.

It is thus an object of the present invention to overcome the aforementioned drawbacks.

Accordingly, we have found a new and improved process for the preparation of an aminopropionitrile of the general formula I

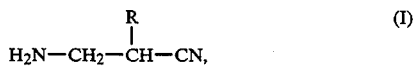

in which R denotes hydrogen or methyl, wherein ammonia is caused to react with an acrylonitrile of the general formula II

In which the substituent has the aforementioned meanings, in a molar ratio of from 1:1 to 500:1 over a heterogenic catalyst at temperatures ranging from 40° to 180° C. and pressures ranging from 10 to 350 bar.

The process of the invention can be carried out as follows:

The reaction can be carried out at temperatures ranging from 40° to 180° C. and pressures ranging from 10 to 350 bar batchwise or, preferably, continuously. The preferred continuous process can be carried out at temperatures ranging from 40° to 150° C. and pressures ranging from 10 to 200 bar and preferably at from 50° to 120° under a pressure of from 150 to 230 bar.

Usually the ammonia used has a content of from 0 to 5 wt % of water and is preferably substantially anhydrous (from 0 to 1 wt % water) and more preferably contains from 0.1 to 1 wt % of water, the molar ratio of said ammonia to the acrylonitriles being from 1:1 to 500:1, preferably from 2:1 to 100:1 and more preferably from 10:1 to 80:1. Any ammonia not converted during the reaction can by recycled to the reaction in a technically simple manner without impairment of the yield of aminopropionitrile (circulating mode).

Generally speaking, no solvents are used, but it is possible to add to the acrylonitrile II, if desired, inert solvents such as ethers eg dibutyl ether, tetrahydrofuran, dimethoxy ether, or eg hydrocarbons such as cyclohexane, benzene, and toluene in amounts of from 0 to 500 wt %, preferably from 50 to 200 wt %.

It is advantageous to maintain in a throughput of from 0.1 to 10 g and preferably from 0.1 to 2 g of acrylonitrile per gram of catalyst per hour.

Suitable heterogenic catalysts are, in particular, acidic and/or basic or amphoterically active oxides of Group VIIb and Group VIIb elements, such as Fe$_2$O$_3$, MnO$_2$, Co$_3$O$_4$, MnO, Re$_2$O$_7$, Fe$_3$O$_4$, CoO, NiO and, preferably, MnO$_2$, Fe$_2$O$_3$, and Co$_3$O$_4$ and more preferably Fe$_2$O$_3$.

Further catalysts for the process of the invention are acidic or basic ion exchangers such as gel-ion exchangers based on styrene such as those bearing the trademarks Lewatit ® or Amberlite ®, macroporous ion exchangers based on styrene such as those bearing the trademark Lewatit ®, macroreticular ion exchangers based on styrene or acrylics such as those bearing the trademark Amberlite ® or macroporous exchangers based on siloxane such as those having the trademark Deloxan ®, more preferably macroporous ion exchangers.

The aminopropionitriles of the general formula I produced by this process are:
3-aminopropionitrile,
3-amino-isobutyronitrile.

The aminopropionitriles of the general formula I produced in the process of the invention are intermediates for the preparation of diamines, aminocarboxylic acids and aminocarboxylamides.

The 3-aminopropionitrile of the general formula I produced in the process of the invention is suitable for use as an intermediate for the preparation of
β-amino acids/alanine as a starting point for the preparation of calcium pantothenate by hydrolysis (DE-A 2,223,236)
1,3-propylenediamine,
which are used in pharmaceuticals, polyamides, and wood preservatives (DE-A 3,248,326, DT 2,004,405)

EXAMPLES

Example 1

A mixture of 210 mL of liquid ammonia and 19 mL of acrylonitrile was pumped through a tubular reactor packed with 51 g of $Fe_2O_3$ (1–2 mm grit) at 50° C. under a pressure of 150 bar (throughput 0.3 g of acrylonitrile $g^{-1}$cat. $h^{-1}$). The conversion rate was 90%. Following an on-stream period of 22 h the effluent had the following composition (quantitative GC analysis)
57.6 wt % of 3-aminopropionitrile
33.1 wt % of bis(2-cyanoethyl)amine
8 wt % of acrylonitrile

Example 2

A mixture of 215 mL of liquid ammonia and 19 mL of acrylonitrile was pumped through a tubular reactor packed with 29 g of acid ion exchanger (Amberlyst 15) at 50° C. under a pressure of 180 bar (throughput 0.53 g of acrylonitrile $g^{-1}$cat. $h^{-1}$). The conversion rate was 99.4%. Following an on-stream period of 20 h, the effluent had the following composition (quantitative GC analysis)
81.0 wt % of 3-aminopropionitrile
18.2 wt % of bis(2-cyanoethyl)amine
0.48 wt % of acrylonitrile

Example 3

A mixture of 215 mL of liquid ammonia and 19 mL of acrylonitrile was pumped through a tubular reactor packed with 36 g of basic ion exchanger (Lewatit MP-600) at 50° C. under a pressure of 180 bar (throughput 0.4 g of acrylonitrile $g^{-1}$cat. $h^{-1}$). The conversion rate was 99.4%. Following an on-stream period of 20 h the effluent had the following composition (quantitative GC analysis)
77.8 wt % of 3-aminopropionitrile
20.2 wt % of bis(2-cyanoethyl)amine
0.48 wt % acrylonitrile

We claim:

1. A process for the preparation of an aminopropionitrile of the formula I

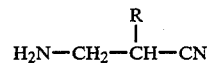

in which R is hydrogen or methyl, which comprises reacting liquid ammonia with an acrylonitrile of the formula II

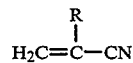

in which R has the above meaning, in a molar ratio of ammonia to acrylonitrile of from 1:1 to 500:1 over a heterogeneous catalyst selected from the group consisting of oxides of elements of Groups VIIb or VIIIb and acidic or basic ion exchangers, at temperatures ranging from 40° to 180° C. and at pressures ranging from 10 to 350 bar.

2. A process for the preparation of an aminopropionitrile as defined in claim 1, wherein R denotes hydrogen.

3. A process for the preparation of an aminopropionitrile as defined in claim 1, wherein the heterogenic catalyst used is an acidic or basic organic ion exchanger.

4. A process for the preparation of an aminopropionitrile as defined in claim 1, wherein ammonia is reacted with the acrylonitrile in a molar ratio of from 10:1 to 80:1.

5. A process for the preparation of an aminopropionitrile as defined in claim 1, wherein the reaction is carried out at temperatures ranging from 50° to 120° C.

6. A process for the preparation of an aminopropionitrile as defined in claim 1, wherein the reaction is carried out at pressures ranging from 150 to 230 bar.

7. A process as claimed in claim 1, wherein the catalyst is selected from the group consisting of the elements of Groups VIIb and VIIIb and mixtures thereof.

8. A process as claimed in claim 1, wherein the liquid ammonia contains up to 5 wt % of water.

9. A process as claimed in claim 1, wherein the liquid ammonia contains from 0.1 to 1 wt % of water.

10. A process claimed in claim 1, wherein the reaction is carried out continuously at a throughput of from 0.1 to 10 grams of acrylonitrile per gram of catalyst per hour.

11. A process as claimed in claim 1 wherein the catalyst is a metal oxide selected from the group consisting of $MnO_2$, $Fe_2O_3$ and $Co_3O_4$.

12. A process as claimed in claim 1 wherein the catalyst is $Fe_2O_3$.

* * * * *